(12) United States Patent
Sternby et al.

(10) Patent No.: US 11,058,810 B2
(45) Date of Patent: Jul. 13, 2021

(54) DETECTION OF A DISRUPTION OF A FLUID CONNECTION BETWEEN TWO FLUID CONTAINING SYSTEMS

(71) Applicant: GAMBRO LUNDIA AB, Lund (SE)

(72) Inventors: Jan Sternby, Lund (SE); Bo Olde, Lund (SE)

(73) Assignee: GAMBRO LUNDIA AB, Lund (SE)

( * ) Notice: Subject to any disclaimer, the term of this patent is extended or adjusted under 35 U.S.C. 154(b) by 310 days.

(21) Appl. No.: 16/098,032

(22) PCT Filed: May 11, 2017

(86) PCT No.: PCT/EP2017/061271
§ 371 (c)(1),
(2) Date: Oct. 31, 2018

(87) PCT Pub. No.: WO2018/001614
PCT Pub. Date: Jan. 4, 2018

(65) Prior Publication Data
US 2019/0143026 A1    May 16, 2019

(30) Foreign Application Priority Data
Jun. 30, 2016 (SE) .................................... 1650944-0

(51) Int. Cl.
*A61M 1/36* (2006.01)
(52) U.S. Cl.
CPC ....... *A61M 1/3656* (2014.02); *A61M 2205/15* (2013.01); *A61M 2205/18* (2013.01);
(Continued)
(58) Field of Classification Search
CPC .............. A61M 1/3656; A61M 1/3639; A61M 2205/15; A61M 2205/18;
(Continued)

(56) References Cited

U.S. PATENT DOCUMENTS 6,090,048 A    7/2000    Hertz et al.
6,663,585 B1   12/2003   Ender
(Continued)

FOREIGN PATENT DOCUMENTS

EP    2712639       4/2014
JP    2010136745    6/2010
(Continued)

OTHER PUBLICATIONS

International Search Report issued in International Patent Application No. PCT/EP2017/061271 dated Aug. 8, 2017.
(Continued)

*Primary Examiner* — Ariana Zimbouski
(74) *Attorney, Agent, or Firm* — K&L Gates LLP (57) ABSTRACT

A monitoring device implements a monitoring method that comprises: activating a first monitoring technique that operates to detect the disruption and generate a corresponding alarm signal while a second monitoring technique is deactivated, obtaining at least one of a first count of false alarms generated by the primary monitoring technique and a second count of false alarms generated by the second monitoring technique if activated, and selectively, based on at least one of the first and second counts, activating the second monitoring technique to operate, instead of or jointly with the first monitoring technique, to detect the disruption and generate the corresponding alarm signal. The monitoring device may be connected to or part of an apparatus for blood treatment and operable to detect a disconnection of an extracorporeal blood circuit from a vascular system of a patient, e.g. a venous-side disconnection.

29 Claims, 5 Drawing Sheets

(52) U.S. Cl.
CPC . *A61M 2205/3331* (2013.01); *A61M 2205/50* (2013.01); *A61M 2230/06* (2013.01)

(58) Field of Classification Search
CPC ...... A61M 2205/3331; A61M 2205/50; A61M 2230/06
See application file for complete search history.

(56) References Cited

U.S. PATENT DOCUMENTS

| | | | |
|---|---|---|---|
| 7,575,562 | B2 | 8/2009 | Oishi et al. |
| 2002/0190863 | A1 | 12/2002 | Lynn |
| 2003/0128125 | A1* | 7/2003 | Burbank ............ A61M 1/3621 340/605 |
| 2003/0194894 | A1 | 10/2003 | Wariar et al. |
| 2003/0195453 | A1 | 10/2003 | Han et al. |
| 2003/0195454 | A1 | 10/2003 | Wariar et al. |
| 2005/0010118 | A1 | 1/2005 | Toyoda et al. |
| 2006/0074369 | A1 | 4/2006 | Oishi et al. |
| 2007/0000847 | A1 | 1/2007 | Ross et al. |
| 2007/0213599 | A1* | 9/2007 | Siejko ..................... A61B 5/00 600/300 |
| 2009/0292236 | A1* | 11/2009 | Kleinekofort ....... A61M 1/3639 604/6.16 |
| 2011/0034814 | A1 | 2/2011 | Kopperschmidt |
| 2011/0080193 | A1 | 4/2011 | Kane et al. |
| 2019/0240392 | A1* | 8/2019 | Sternby ............... A61M 1/3656 |

FOREIGN PATENT DOCUMENTS

| | | |
|---|---|---|
| KR | 2013-0003597 | 1/2013 |
| WO | WO0147581 | 7/2001 |
| WO | WO2009122229 | 10/2009 |
| WO | WO2009156174 | 12/2009 |
| WO | WO2009156175 | 12/2009 |
| WO | WO2010149726 | 12/2010 |
| WO | WO2012175267 | 12/2012 |
| WO | WO2013000777 | 1/2013 |
| WO | WO2014009111 | 1/2014 |
| WO | WO2014095524 | 6/2014 |

OTHER PUBLICATIONS

Written Opinion issued in International Patent Application No. PCT/EP2017/061271 dated Aug. 8, 2017.

* cited by examiner

DETECTION OF A DISRUPTION OF A FLUID CONNECTION BETWEEN TWO FLUID CONTAINING SYSTEMS

PRIORITY CLAIM

The present application is a National Phase of International Application No. PCT/EP2017/061271, filed on May 11, 2017, which claims priority to Swedish Patent Application No. 1650944-0, filed on Jun. 30, 2016, the entire contents of each of which are being incorporated herein by reference.

TECHNICAL FIELD

The present invention relates to a technique for detecting a disruption of a fluid connection between two fluid containing systems, based on at least one measurement signal generated by a sensor arranged in or associated with one of the fluid containing systems. The fluid connection may be established between an extracorporeal circuit for blood processing and the vascular system of a human subject.

BACKGROUND ART

In extracorporeal blood processing, blood is taken out of a human subject, processed (e.g. treated) and then reintroduced into the subject by means of an extracorporeal blood flow circuit ("EC circuit") which is part of a system or machine for blood processing. Generally, the blood is circulated through the EC circuit by a blood pump. In certain types of extracorporeal blood processing, the EC circuit includes an access device for blood withdrawal (e.g. an arterial needle or catheter) and an access device for blood reintroduction (e.g. a venous needle or catheter), which are inserted into a dedicated blood vessel access (e.g. fistula, graft or catheter) on the subject. The access devices form a fluid connection between the EC circuit and the cardiovascular system of the subject. This type of EC circuit is, e.g., used in extracorporeal blood treatments such as hemodialysis, hemodiafiltration, hemofiltration, plasmapheresis, bloodbanking, blood fraction separation (e.g. cells) of donor blood, apheresis, extracorporeal blood oxygenation, assisted blood circulation, extracorporeal liver support/dialysis, ultrafiltration, heart congestion failure treatment, etc.

It is vital to minimize the risk for malfunctions in the fluid connection that may lead to a potentially life-threatening condition of the subject. A particularly serious condition may arise if the EC circuit is disrupted downstream of the blood pump while the blood pump is running, e.g. by the access device for blood reintroduction coming loose from the blood vessel access. Such a venous-side disruption, which is commonly referred to as a Venous Needle Dislodgement (VND), may cause the subject to be drained of blood within minutes. A disruption on the arterial side, e.g. by the access device for blood withdrawal coming loose from the blood vessel access, may also present a patient risk, by air being sucked into the EC circuit and transported into the cardiovascular system, causing air embolism.

Machines for extracorporeal blood treatment typically include a safety system that monitors the status of the fluid connection between the EC circuit and the subject and triggers an alarm and/or an appropriate safety action whenever a potentially dangerous situation is detected. In dialysis machines, it is common for such safety systems to operate on a pressure signal from a pressure sensor in the EC circuit, where the fluid pressure measured by the pressure sensor is responsive to a disconnection of the EC circuit from the blood vessel access. For example, the pressure sensor may be arranged to measure the pressure level on the venous side of the EC circuit. A venous-side disconnection results in a changed venous-side pressure, which may be detected by comparing the measured pressure level with one or more alarm thresholds that define a predefined, allowable pressure range.

Over time, a large number of alternative techniques have been proposed for monitoring of the status of the fluid connection between the EC circuit and the subject. Such other techniques may involve detecting pressure waves that have propagated via the fluid connection to a pressure sensor in the EC circuit, applying a blood leakage sensor onto the vascular access to detect presence of wetness or blood, operating an optical sensor attached to the patient to detect a perturbation transmitted from the apparatus to the patient via the fluid connection, analyzing an image signal from a camera directed to the vascular access, electrically detecting a disconnection of the access device from the vascular access, etc.

When implemented in the safety system of a machine for extracorporeal blood treatment, the monitoring of the fluid connection is first and foremost designed to avoid false negatives, i.e. missed alarm conditions, and thus inevitably results in generation of false positives, i.e. false alarms. At the same time, it is important to avoid frequent false alarms that require the attention of dialysis personnel.

Thus, it is a challenge to design the safety system so as to detect all potentially dangerous situations without simultaneously generating a large number of false alarms.

Although the foregoing description is given in the context of extracorporeal blood processing, it is understood that a corresponding need to detect a disruption of a fluid connection between two fluid containing systems may arise in other fields of technology.

SUMMARY

It is an objective of the invention to at least partly overcome one or more of limitations of the prior art.

Another objective is to provide a technique for detecting a disruption of a fluid connection between two fluid containing systems.

Yet another objective is to provide such a technique that reduces the risk for false positives.

A further objective is to provide such a technique which is applicable for detecting a return-side disconnection of an extracorporeal blood circuit from the vascular system of a subject.

One or more of these objectives, as well as further objectives that may appear from the description below, are at least partly achieved by a monitoring device, an apparatus for extracorporeal blood processing, a method of detecting a disruption, a method of controlling a monitoring device, and a computer-readable medium according to the independent claims, embodiments thereof being defined by the dependent claims.

A first aspect of the invention is a monitoring device. The monitoring device comprises an input interface for receiving one or more measurement signals from one or more sensors arranged in or associated with a first fluid containing system and/or a second fluid containing system, the one or more measurement signals being responsive to a disruption of a fluid connection between the first fluid containing system and the second fluid containing system. The monitoring device further comprises a first disruption detector and a second disruption detector, each being configured to operate a respective detection logic on at least one of the one or more measurement signals to detect apparent disruptions of the fluid connection and provide alarm indications corresponding to the apparent disruptions, and an alarm module for generating an alarm signal based on the alarm indications. The monitoring device further comprises a switching module configured to operate the monitoring device in one of a first mode, in which at least the first disruption detector is operated and the alarm signal is generated based only on the alarm indications provided by the first disruption detector, and a second mode, in which at least the second disruption detector is operated and the alarm signal is based at least on the alarm indications provided by the second disruption detector, wherein the switching module is further configured to, when operating the monitoring device in the first mode, obtain at least one of a first count of false alarm indications provided per unit time by the first disruption detector and a second count of false alarm indications provided per unit time by the second disruption detector, and selectively, based on at least one of the first and second counts, switch the monitoring device to the second mode.

The first aspect is based on the insight that the number of false alarm indications may be used as a quality indicator of the performance of the first and/or second disruption detectors and that the overall performance of the monitoring device may be improved by switching between two detection techniques, implemented by the first and second disruption detectors, based on this quality indicator. By suitable selection of detection techniques, it is possible to compensate for weaknesses of the first disruption detector that result in false alarm indications at certain operating conditions, by selectively switching to generating the alarm signal based at least on alarm indications provided by the second disruption detector.

The false alarms may be identified to the monitoring device by manual input, e.g. by an operator assessing whether each alarm indication during the first mode corresponds to an actual alarm situation or not, and by the operation signaling each false alarm to the monitoring device. However, the monitoring device is preferably configured to execute an automatic validation to autonomously identify false alarms among the alarm indications provided by the first and/or second disruption detectors.

Embodiments involving the validation and other features of the monitoring device are defined below and may serve the purpose of reducing the number of false positives, improving robustness, facilitating implementation, or another purpose as understood by the skilled person.

In one embodiment, the switching module is configured to switch the monitoring device from the first mode to the second mode when the first count exceeds a predefined first limit and/or when the second count is below a predefined second limit. Alternatively or additionally, the switching module may be further configured to, when operating the monitoring device in the second mode, operate the first disruption detector and the second disruption detector to provide the alarm indications, obtain at least one of the first and second counts, and selectively, based on said at least one of the first and second counts, switch the monitoring device to the first mode. Further, the switching module may be configured to selectively switch the monitoring device from the second mode to the first mode when the first count is below a predefined second limit and/or when the second count exceeds a predefined fourth limit.

In one embodiment, the switching module is configured to operate the monitoring device in the second mode so that the alarm signal is generated based only on the alarm indications provided by the second disruption detector.

In an alternative embodiment, the switching module is configured to operate the monitoring device in the second mode so that the alarm signal is generated based on the alarm indications provided by the second disruption detector and the alarm indications provided by the first disruption detector.

In one embodiment, each of the first and second disruption detectors is configured to, when operating the respective detection logic, generate a time-sequence of parameter values of a detection parameter to represent a time segment in the at least one measurement signal, compare the time-sequence of parameter values to an allowable range, and provide the alarm indications when a predefined number of parameter values in the time-sequence of parameter values fall outside the allowable range.

In one embodiment, the detection logics of the first and second disruption detectors differ by at least one of: the at least one measurement signal, preprocessing of said at least one measurement signal, the detection parameter, the current allowable range, and the predefined number of parameter values.

In one embodiment, the second disruption detector is configured to obtain the at least one measurement signal from at least one pressure sensor in the first fluid containing system, and generate the time-sequence of parameter values to be indicative of a pressure level in the first fluid containing system.

In one embodiment, the first disruption detector is configured to obtain the at least one measurement signal from at least one pressure sensor in the first fluid containing system, and generate the time-sequence of parameter values to represent pulsations originating from a pulse generator in or associated with the second fluid containing system.

In one embodiment, the first disruption detector is further configured to perform an automatic validation of each alarm indication to determine the alarm indication as a false alarm indication or a true alarm indication, and the monitoring device further comprises a false alarm analyzer configured to produce the first count based on the false alarm indications determined by the automatic validation. Further, the automatic validation may involve one or more of: obtaining and processing a further measurement signal among the one or more measurement signals; generating parameter values of another detection parameter as a function of the at least one measurement signal; and intermittently disabling one or more sources of signal interferences in the at least one measurement signal. Alternatively or additionally, the first fluid containing system may comprise a blood processing apparatus for connection, by the fluid connection, to a subject, the one or more sensors may comprise a pressure sensor for sensing a pressure of blood in the blood processing apparatus, and the automatic validation may comprise: obtaining and processing the at least one measurement signal for detection of pulsations originating from a pulse generator in or associated with the subject. Further, the automatic validation may comprise, before obtaining and processing the at least one measurement signal, generating a control signal to stop one or more pumping devices arranged in the blood processing apparatus.

In one embodiment, the alarm module is configured to generate the alarm signal based on the true alarm indications.

A second aspect of the invention is an apparatus for extracorporeal blood processing. The apparatus comprises: an extracorporeal blood circuit for connection in fluid communication with the vascular system of a patient at first and second ends and comprising a blood pump for circulating blood from the first end through a blood processing device to the second end; at least one sensor configured to generate at least one measurement signal which is responsive to a disconnection of the extracorporeal blood circuit from the vascular system of the patient downstream of the blood pump; a first disruption detector and a second disruption detector, each being configured to operate a respective detection logic on at least one of the one or more measurement signals to detect the disconnection and provide an alarm indication corresponding to the disconnection, and an alarm module for generating an alarm signal based on the alarm indication. The apparatus further comprises a switching module configured to operate the monitoring device in one of a first mode, in which at least the first disruption detector is operated and the alarm signal is generated based only on the alarm indication provided by the first disruption detector, and a second mode, in which at least the second disruption detector is operated and the alarm signal is generated based at least on the alarm indication provided by the second disruption detector, wherein the switching module is further configured to, when operating the monitoring device in the first mode, obtain at least one of a first count of false alarm indications provided per unit time by the first disruption detector and a second count of false alarm indications provided per unit time by the second disruption detector, and selectively, based on at least one of the first and second counts, switch the monitoring device to the second mode.

A third aspect of the invention is a method of detecting a disruption of a fluid connection between two fluid containing systems. The method comprises: activating a first monitoring technique that operates to detect the disruption and generate a corresponding alarm signal while a second monitoring technique is deactivated; obtaining at least one of a first count of false alarms generated by the first monitoring technique and a second count of false alarms generated by the second monitoring technique if activated; and selectively, based on at least one of the first and second counts, activating the second monitoring technique to operate, instead of or jointly with the first monitoring technique, to detect the disruption and generate the corresponding alarm signal.

In one implementation, the second monitoring technique is selectively activated when the first count exceeds a predefined first limit and/or when the second count is below a predefined second limit.

In one embodiment, the method further comprises: selectively, based on at least one of the first and second counts, deactivating the second monitoring technique.

In one implementation, the second monitoring technique is selectively deactivated when the first count is below a predefined third limit and/or when the second count exceeds a predefined fourth limit.

In one embodiment, the method further comprises: setting the first monitoring technique into a silent state while the second monitoring technique is activated, the silent state causing the first monitoring technique to operate to detect the disruption without generating the corresponding alarm signal, and the method further comprises: evaluating if a respective disruption detected by the first monitoring technique in the silent mode represents a false alarm and updating the first count accordingly.

In one embodiment, the second monitoring technique, when deactivated, is set into a silent state in which the second monitoring technique operates to detect the disruption without generating the corresponding alarm signal, and the method further comprises: evaluating if a respective disruption detected by the second monitoring technique in the silent mode represents a false alarm and updating the second count accordingly.

In one embodiment, the method further comprises: validating a respective disruption detected by the first monitoring technique to identify the respective disruption as a false alarm indication or a true alarm indication, and generating the first count based on the thus-identified false alarm indications. Further, the validating may comprise: intermittently stopping operation of one or more devices in the first and/or second fluid containing system, said devices causing, when operating, signal interferences in one or more measurement signals that are processed by the first monitoring technique for detection of the disruption.

In one embodiment, the method further comprises: validating a respective disruption detected by the second monitoring technique to identify the respective disruption as a false alarm indication or a true alarm indication, and generating the first count based on the thus-identified false alarm indications.

In one embodiment, each of the first and second monitoring techniques operates on one or more measurement signals from one or more sensors arranged in or associated with the first fluid containing system and/or the second fluid containing system, the one or more measurement signals being responsive to the disruption of the fluid connection, and the method further comprises: obtaining the one or more measurement signals.

In one embodiment, the method further comprises: obtaining at least one pressure signal from at least one pressure sensor in the first fluid containing system, wherein the first monitoring technique, to detect the disruption, operates on the at least one pressure signal to generate a time-sequence of parameter values that represent pulsations originating from a pulse generator in or associated with the second fluid containing system, and compares the parameter values to an allowable range.

In one embodiment, the method further comprises: obtaining at least one pressure signal from at least one pressure sensor in the first fluid containing system, wherein the second monitoring technique, to detect the disruption, operates on the at least one pressure signal to generate a time-sequence of parameter values that are indicative of a pressure level in the first fluid containing system, and compares the parameter values to an allowable range.

A fourth aspect of the invention is a method of controlling a monitoring device comprising a processor. The method is executed by the processor in the monitoring device and comprises: obtaining one or more measurement signals from one or more sensors arranged in or associated with a first fluid containing system and/or a second fluid containing system, said one or more measurement signals being responsive to a disruption of a fluid connection between the first fluid containing system and the second fluid containing system; generating, in a first operating mode of the monitoring device, an alarm signal based only on alarm indications provided by a first detection logic when operated on at least one of the one or more measurement signals to detect apparent disruptions of the fluid connection; obtaining, when operating the monitoring device in the first mode, at least one of a first count of false alarm indications provided per unit time by the first detection logic and a second count of false alarm indications provided per unit time by a second detection logic; and selectively, based on at least one of the first and second counts, switching the monitoring device to a second mode, in which the alarm signal is generated based at least on alarm indications provided by the second detection logic.

A fifth aspect of the invention is a computer-readable medium comprising processing instructions for causing a data processor to perform the method of the third or fourth aspect.

Any one of the above-identified embodiments of the first aspect may be adapted and implemented as an embodiment of the second to fifth aspects.

Still other objectives, features, aspects and advantages of the present invention will appear from the following detailed description, from the attached claims as well as from the drawings.

DETAILED DESCRIPTION OF EXAMPLE EMBODIMENTS

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure may satisfy applicable legal requirements. Like numbers refer to like elements throughout.

Also, it will be understood that, where possible, any of the advantages, features, functions, devices, and/or operational aspects of any of the embodiments of the present invention described and/or contemplated herein may be included in any of the other embodiments of the present invention described and/or contemplated herein, and/or vice versa. In addition, where possible, any terms expressed in the singular form herein are meant to also include the plural form and/or vice versa, unless explicitly stated otherwise. As used herein, "at least one" shall mean "one or more" and these phrases are intended to be interchangeable. Accordingly, the terms "a" and/or "an" shall mean "at least one" or "one or more," even though the phrase "one or more" or "at least one" is also used herein. As used herein, except where the context requires otherwise owing to express language or necessary implication, the word "comprise" or variations such as "comprises" or "comprising" is used in an inclusive sense, that is, to specify the presence of the stated features but not to preclude the presence or addition of further features in various embodiments of the invention.

Figure 1:
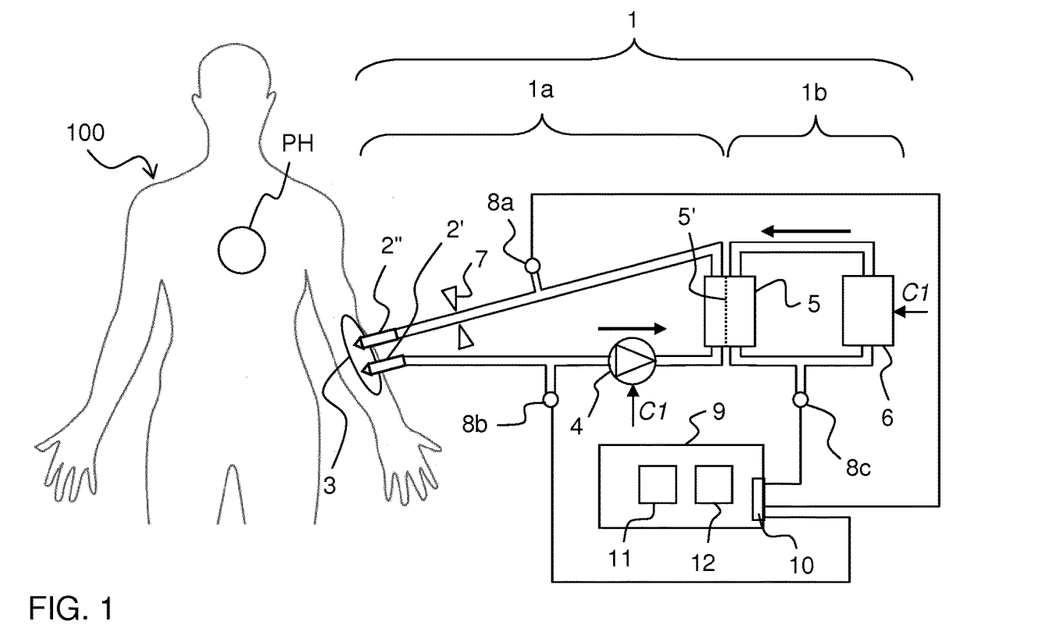
FIG. 1 is a schematic diagram of an extracorporeal blood processing apparatus attached to a human subject and comprising a monitoring device for disruption detection.

Embodiments of the invention will be exemplified with reference to an apparatus 1 for blood treatment, which is schematically depicted in FIG. 1. In the following example, the apparatus 1 is assumed to be a dialysis system which is formed by a blood line set attached to a dialysis machine or monitor, as is well known in the art. FIG. 1 illustrates a human subject or patient 100 which is connected to an extracorporeal blood flow circuit 1a by way of access devices 2', 2" inserted into a dedicated vascular access 3 (also known as "blood vessel access") on the patient. The extracorporeal blood flow circuit 1a (denoted "EC circuit" in the following) is configured to communicate blood to and from the cardiovascular system of the patient. In the illustrated example, a blood pump 4 is operable to draw blood from the vascular access 3 via an access device 2' for blood withdrawal and to pump the blood through a blood treatment unit 5 and back to the vascular access 3 via an access device 2" for blood return. Thus, when both access devices 2', 2" are connected to the vascular access 3, the EC circuit 1a defines a blood path that starts and ends at the vascular access 3. The EC circuit 1a may be seen to comprise a "venous side" which is the part of the blood path located downstream of the blood pump 4, and an "arterial side" which is the part of the blood path located upstream of the blood pump 4. The blood pump 4 may be of any type, e.g. a rotary peristaltic pump, a linear peristaltic pump, a diaphragm pump, or a centrifugal pump.

The blood treatment unit 5 may be any type of blood filtration device, such as a coil dialyzer, a parallel plate dialyzer, a hollow fiber dialyzer, etc. For simplicity, the blood treatment unit 5 is denoted "dialyzer" in the following. The dialyzer 5 has a blood side and a treatment fluid side separated by a semipermeable membrane 5'. The blood side is connected as part of the EC circuit 1a, and the treatment fluid side is connected as part of a supply system 1b for treatment fluid (denoted "TF circuit" in the following). The TF circuit 1b is arranged to pump a treatment fluid through the treatment fluid side of the dialyzer 5, whereby solutes are transported over the membrane 5' due to a concentration gradient and/or ultrafiltrate is transported over the membrane 5' due to a pressure gradient. The skilled person understands that the TF circuit 1b may include a plurality of functional components such as a source of fresh treatment fluid, a receptacle/drain for spent treatment fluid, one or more pumps, balancing chambers, valves, heaters, conductivity sensors, etc. For simplicity, these components are collectively represented by a generic box 6 in FIG. 1.

In the example of FIG. 1, a clamp 7 is arranged on the venous side of the EC-circuit 1a. Although not shown, a corresponding clamp may be arranged on the arterial side. The clamp(s) 7 may be operated to block fluid passage through the blood lines, e.g. before and after a treatment session, or as part of the apparatus entering a safe state following detection of an alarm condition.

It is understood that the EC circuit 1a and the TF circuit 1b form part of the above-mentioned apparatus 1 for blood treatment. A main control unit (not shown) in the apparatus 1 may control and synchronize the operation of, e.g., the blood pump 4, the components 6, the clamp(s) 7, as well as further components such as pumps, sensors, valves, a user interface, etc.

The EC circuit 1a includes a pressure sensor or transducer 8a (denoted "venous pressure sensor" or "venous sensor") on the venous side of the EC circuit 1a, downstream of the dialyzer 5, a pressure sensor or transducer 8b (denoted "arterial pressure sensor" or "arterial sensor") on the arterial side of the EC circuit 1a. The venous and arterial sensors 8a, 8b provide a respective time-varying signal that represents the pressure in the blood on the venous side ("venous signal") and the arterial side ("arterial signal"), respectively.

In the example of FIG. 1, a pressure sensor or transducer 8c (denoted "TF pressure sensor" or "TF sensor") is also arranged in the TF circuit 1b to provide a time-varying signal that represents the pressure in the treatment fluid. The TF sensor 8c may have any placement in the TF circuit 1b, e.g. downstream (as in FIG. 1) or upstream of the dialyzer 5.

Generally, the EC circuit 1a and the TF circuit 1b may be seen to define a fluid containing system, which is connected to another fluid containing system constituted by the cardiovascular system of the patient 100. A monitoring device 9 is arranged to detect a disruption of a fluid connection between the fluid containing systems, typically during ongoing blood treatment. When detecting a (potential) malfunction, the device 9 may issue an alarm or warning signal to alert an operator of the apparatus 1 and/or cause the main control unit of the apparatus 1 to take appropriate action. The device 9 may be included as part of the apparatus 1 for blood treatment, and may be connected to or part of the above-mentioned main control unit. Alternatively, the device 9 is separate from the apparatus 1.

Depending on implementation, the monitoring device 9 may be configured to detect a disruption occurring on the venous side of the EC circuit 1a and/or on the arterial side of the EC circuit 1a. The disruption may correspond to a disconnection of the EC circuit 1a from the cardiovascular system and may be caused, e.g., by a dislodgement of the respective access device 2', 2" from the vascular access 3, a rupture of a blood line in the EC circuit 1a, or a disconnection of a connector (not shown) which may be installed between the respective access device 2', 2" and the blood line. Techniques for detecting a disconnection on the venous-side of the EC circuit 1a are denoted "VND techniques" herein. Additionally or alternatively, the monitoring device 9 may be configured to detect a disruption caused by other malfunctions of the EC circuit 1a, e.g. that a blood line is kinked, or that the respective access device 2', 2" is positioned too close to, or inserted into, a wall of the blood vessel access 3 (known as "infiltration").

The monitoring device 9 comprises a signal interface 10 for receiving measurement signal(s) from one or more appropriate sensors, and processing circuitry 11, 12 for processing the measurement signal(s) for the purpose of detecting the disruption of the fluid connection. In the example of FIG. 1, the monitoring device is connected to receive and process the pressure signals from the pressure sensors 8a, 8b, 8c for disruption detection. However, it should be noted that the monitoring device 9 may be implemented to utilize any available techniques for detecting a disruption. Thus, the monitoring device 9 may operate on any number of measurement signals from any type of sensors, provided that at least one of the measurement signals is responsive to the disruption to be detected. As used herein, "responsive to" indicates that the disruption results in a change in the measurement signal. For example, such a measurement signal may be a pressure signal from a pressure sensor in the apparatus, a signal from a blood leakage sensor attached onto the vascular access to detect presence of wetness or blood, a signal from an optical sensor attached to the patient to detect a perturbation transmitted from the apparatus to the patient via the fluid connection, a signal from an electrical disconnection sensor, an image signal from a camera directed to the vascular access, etc. The signal from the optical sensor may e.g. be processed for disruption detection in accordance with WO2009/122229. The electrical disconnection sensor may be configured to measure electrical current, voltage, capacitance, or an equivalent quantity, e.g. as disclosed in any one of WO01/47581, U.S. Pat. No. 6,663,585, US2003/0194894, US2003/0195453, US2003/0195454 and US2007/0000847.

As will be explained in further detail below, embodiments of the monitoring device 9 are configured to, while applying a first technique for disruption detection, selectively activate a second technique for disruption detection, based on a count of the false alarms that are produced by the first technique and/or a count of the false alarms that are estimated to be produced by the second technique.

Embodiments of the invention may e.g. be at least partly implemented by software instructions that are supplied on a computer-readable medium for execution by a processor 11 in conjunction with an electronic memory 12 in the device 9.

Figure 2:
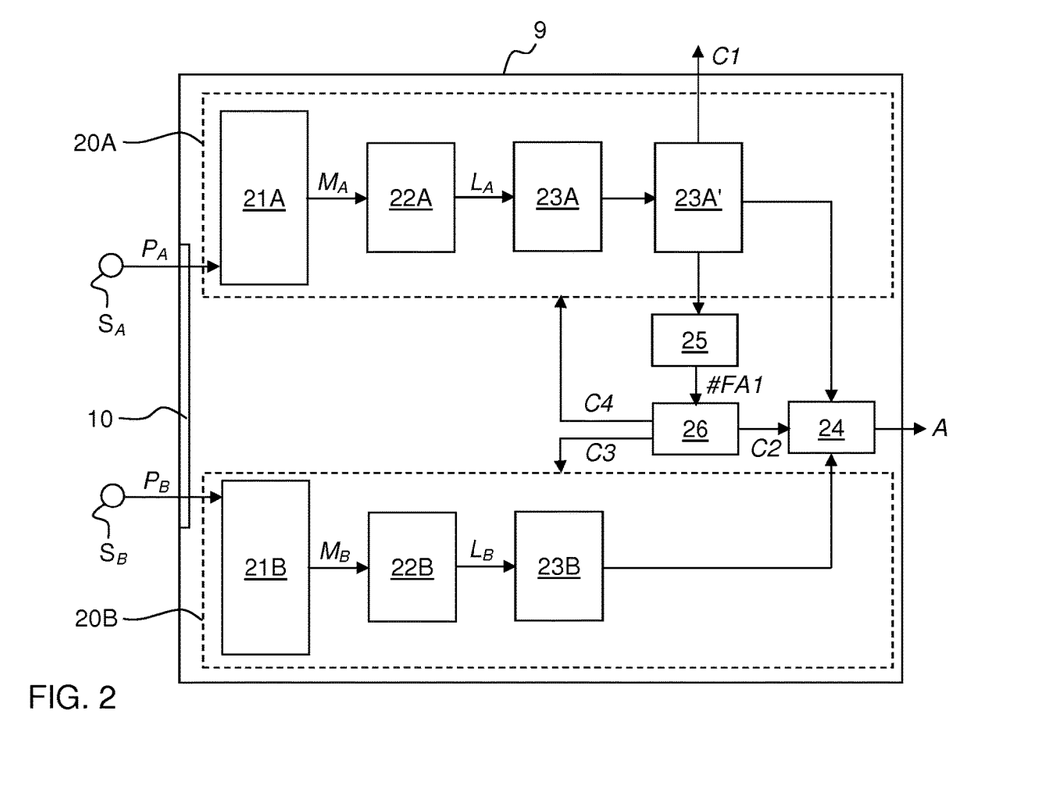
FIG. 2 is a block diagram of the monitoring device in FIG. 1 according to an embodiment.

FIG. 2 illustrates an embodiment of the monitoring device 9 for disruption detection. In the illustrated example, the device 9 is connected by the signal interface 10 to two sensors $S_A$, $S_B$ to acquire measurement signals $P_A$, $P_B$ which are responsive to the disruption to be detected. The sensors $S_A$, $S_B$ may be any one of the sensors discussed in the foregoing. The device 9 comprises modules or blocks that implement a respective functionality. The respective module may be implemented by hardware circuitry, by software executed by the processor 11, or by a combination of hardware circuitry and software.

The device 9 comprises first and second disruption detection modules 20A, 20B ("disruption detectors") which are configured to operate a respective detection logic on a respective measurement signal $P_A$, $P_B$ to detect an apparent disruption of the fluid connection and generate an alarm indication corresponding to the apparent disruption. As used herein, "detection logic" is a definition of the configuration of the respective disruption detector 20A, 20B and the steps to be executed for processing the measurement signal $P_A$, $P_B$ and for deciding if there is an apparent disruption of the fluid connection. The first and second disruption detectors 20A, 20B apply different detection logics and thereby implement different techniques for disruption detection, in a broad sense.

It should be noted that the use of a respective measurement signal $P_A$, $P_B$ by the disruption detectors 20A, 20B is only given as an example. It is conceivable that the disruption detectors 20A, 20B operate on the same measurement signal and/or on more than one measurement signal each.

In the example of FIG. 2, the respective disruption detector 20A, 20B comprises a preprocessing sub-module 21A, 21B ("preprocessor") which is configured to generate a time-varying monitoring signal $M_A$, $M_B$ based on the time-varying measurement signal $P_A$, $P_B$. The preprocessors 21A, 21B may be configured to process the respective measurement signal $P_A$, $P_B$ by, e.g., AD conversion, signal amplification, and removal of offset, high frequency noise and supply voltage disturbances. The preprocessors 21A, 21B may also process the respective measurement signal $P_A$, $P_B$ by any known signal filtering technique for suppression of signal artefacts that originate from the apparatus 1 and/or the patient 100. For example, a measurement signal that is generated by a pressure sensor in the apparatus 1 may contain strong signal artefacts ("pump pulses") that originate from the blood pump 4, as well as signal artefacts that originate from the TF circuit 1b, e.g. from balancing chambers, pumps, valves, etc. Examples of such signal filtering techniques are found in WO2009/156175, WO2010/149726, WO2013/000777, WO2014/009111 and WO2014/095524. It should be noted that the respective preprocessor 21A, 21B may be configured to generate the monitoring signal $M_A$, $M_B$ based on a combination of (filtered) measurement signals, e.g. as a (weighted) difference or sum of two signals.

The respective disruption detector 20A, 20B further comprises a parameter computation sub-module 22A, 22B ("extractor") which is configured to process the time-varying monitoring signal $M_A$, $M_B$ for generation of parameter values of at least one detection parameter. The respective parameter extractor 22A, 22B thereby produces a time-sequence of parameter values $L_A$, $L_B$ that represents or corresponds to a time segment in the respective measurement signal $M_A$, $M_B$.

The respective disruption detector 20A, 20B further comprises a parameter analysis sub-module 23A, 23B ("analyzer"), which is configured to process the time-sequence of parameter values $L_A$, $L_B$ for detection of a possible disruption. In one embodiment, the respective analyzer 23A, 23B is configured to compare the time-sequence of parameter values $L_A$, $L_B$ to an allowable range and generate an alarm indication when an alarm criterion is fulfilled. For example, the alarm criterion may be fulfilled when a predefined number of parameter values $L_A$, $L_B$ (either consecutive or during a given time period) are found to fall outside the allowable range. The predefined number may be any positive number. The range may be defined between two limits. Alternatively, the range may be defined by a single limit, so as to include all parameter values above or below this single limit.

The disruption detector 20A further comprises a validation sub-module 23A', which is configured to perform an automatic validation of each alarm indication produced by the analyzer 23A. In the validation, the respective alarm indication is classified as "false" or "true", i.e. unlikely to represent a disruption and likely to represent a disruption, respectively. The validation sub-module 23A' performs the automatic validation by invoking a change to the operation of the disruption detector 20A and/or to the operation of the apparatus 1, and by evaluating the resulting output of the analyzer 23A. If the analyzer 23A again produces an alarm indication after this change, the validation sub-module 23A' may conclude that the alarm indication is a true alarm indication.

The change to the operation of the disruption detector 20A may involve causing sub-modules 21A-23A to obtain and process another measurement signal from another sensor in the apparatus 1 or on the patient 100 and/or causing the extractor 22A to generate parameter values for another detection parameter as a function of the measurement signal $P_A$.

The change to the operation of the apparatus 1 may involve intermittently disabling one or more sources of signal interferences in the measurement signal $P_A$. In FIG. 2, the validation sub-module 23A' generates a control signal C1 to disable these sources (or triggers the main control unit to generate such a control signal). In the example of FIG. 1, where the measurement signal $P_A$ is a pressure signal from one of the pressure sensors 8a-8c, sources of signal interferences include the blood pump 4 and possibly components of the TF circuit 1b, such as valves, pumps, balancing chambers etc (designated by 6 in FIG. 1).

It is conceivable that the disruption detector 20B includes a corresponding validation sub-module. However, in the example of FIG. 2, the validation sub-module is omitted and all alarm indications generated by the analyzer 23B are presumed to be true.

The monitoring device 9 of FIG. 2 further comprises an alarm module 24, which is configured to generate an alarm signal A based on alarm indications generated by the disruption detectors 20A, 20B. The alarm signal A may activate an alarm in the form of an audible and/or visible signal or message to alert a caretaker of a malfunction of the apparatus 1. The alarm signal A may also cause the main control unit of the apparatus 1 to enter a safe state, e.g. by closing the clamp 7 and stopping the blood pump 4.

The alarm module 24 is configured to only generate the alarm signal A for each alarm indication that is classified as true ("true alarm indications"), whereas the other alarm indications ("false alarm indications" or "false alarms") result in no action by the alarm module 24 and are thus hidden to the user. Different implementations of the alarm module 24 are conceivable. In one implementation, the alarm module 24 is operable to only respond to true alarm indications from one of the disruption detectors 20A, 20B at a time, even if both disruption detectors 20A, 20B are active simultaneously to produce true alarm indications. The alarm module 24 may be controlled to switch between processing true alarm indications from the disruption detector 20A and true alarm indications from the disruption detector 20B by a dedicated control signal C2 (see below). In another implementation, the alarm module 24 is configured to generate the alarm signal for all true alarm indications that are generated by the disruption detectors 20A, 20B. In yet another implementation, the alarm module 24 is configured to apply a combination logic to true alarm indications from the disruption detectors 20A, 20B, e.g. an AND logic that only generates the alarm signal A if both disruption detectors 20A, 20B produce true alarm indications within given time period.

The monitoring device 9 further comprises a false alarm analysis module 25 ("FA analyzer"), which is configured to produce a count #FA1 of false alarms generated per unit time by the disruption detector 20A when operating on the measurement signal $P_A$. Thus, the FA analyzer 25 produces the count #FA1 based on the false alarms that are detected by the validation sub-module 23A'. The FA analyzer 25 may be configured to produce the count #FA1 to include one false alarm indication for each coherent time period in which the alarm criterion is fulfilled and the fluid connection is not disrupted. Thus, the count #FA is generated to represent the number of intermittent time periods with an incorrectly (falsely) fulfilled alarm condition. In an alternative, the FA analyzer 25 is instead configured to produce the count #FA1 to include false alarm indications for all time steps within each of the above-mentioned coherent time periods. Thus, in this alternative, the count #FA is effectively generated to represent the total length of coherent time periods with an incorrectly fulfilled alarm condition.

The FA analyzer 25 may obtain the count #FA1 by incrementing a counter for each false alarm that is identified during a counting time period, and by dividing the resulting number by the extent of the counting time period in any time frame, e.g. seconds, minutes, hours, number of data samples, etc. Alternatively, if the counting time period is fixed, the resulting number may be used as the count #FA1 without normalization by time, since the resulting number is effectively a count per unit time.

It is to be understood that, in embodiments with a validation sub-module in the disruption detector 20B, the FA analyzer 25 may also operate to produce a corresponding count (#FA2) of false alarm indications generated per unit time by the disruption detector 20B when operating on the measurement signal $P_B$.

The monitoring device 9 further comprises a switching module 26, which is configured to selectively set the monitoring device 9 in different monitoring modes based on the count #FA1, and possibly the count #FA2 (if generated). The monitoring modes differ by the origin of the true alarm indications that cause the alarm signal A to be generated. In a first (default) mode, the alarm signal A is generated for true alarm indications produced by the disruption generator 20A and not true alarm indications produced by the disruption generator 20B (if any). In a second mode, the alarm signal A is generated at least for true alarm indications produced by the disruption generator 20B. Depending on implementation of the second mode, as further exemplified below with reference to FIGS. 3A-3C and FIG. 4, the alarm signal may be generated only for true alarm indications produced by the disruption detector 20B, for all true alarm indications produced by the disruption detectors 20A, 20B or by a logic combination of the true alarm indications produced by the disruption detectors 20A, 20B. To switch between the modes, the switching module 26 may generate one or more dedicated control signals C2-C4 (or cause the main control unit to generate the respective control signal). In the example of FIG. 2, the control signal C2 may be generated to set the alarm module 24 to respond to true alarm indications from either the disruption detector 20A (first mode), the disruption detector 20B (second mode), or both of the disruption detectors 20A, 20B (second mode). As an alternative, the control signal C3 may be generated to set the monitoring device 9 in the first mode by deactivating the disruption detector 20B, so as to stop the disruption detector 20B from providing true alarm indications to the alarm module 24. Similarly, the control signal C4 may be generated to set the monitoring device 9 in the second mode by deactivating the disruption detector 20A, so as to stop the disruption detector 20A from providing true alarm indications to the alarm module 24.

As understood from the foregoing, the monitoring device 9 is switched between a first mode, in which only a first monitoring technique is active to result in the alarm signal A, and a second mode, in which a second monitoring technique, optionally in combination with the first monitoring technique, is active to result in the alarm signal A. The switching generally increases the overall performance of the monitoring device 9, by reducing the number of false positives and possibly also reducing the risk for false negatives, compared to a monitoring device that is configured to execute only one of the first and second monitoring techniques for disruption detection. Suitably, the first and second monitoring techniques are selected to be partly complementary, in the sense that they have different weaknesses. Thus, second monitoring technique is suitably capable of operating properly for disruption detection in situations that are known to cause problems for the first monitoring technique, and vice versa.

Figure 3A:
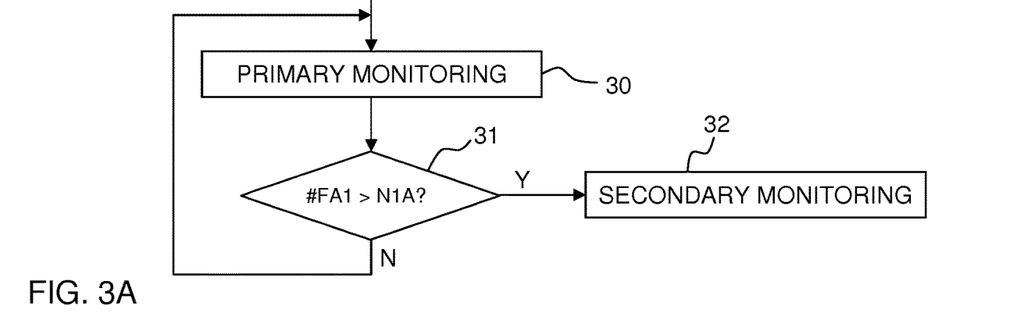
FIGS. 3A-3D are flow charts of monitoring processes executed by the monitoring device of FIG. 2 in different embodiments.
Figure 3B:
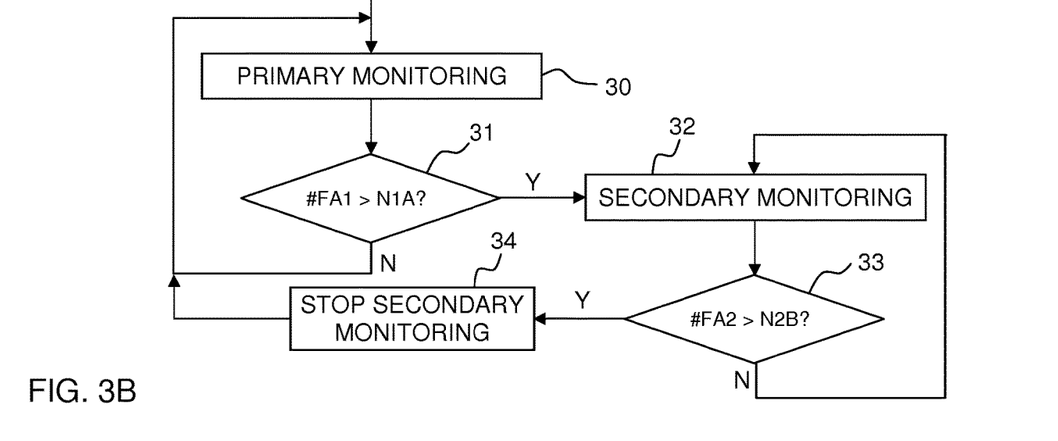
Figure 3C:
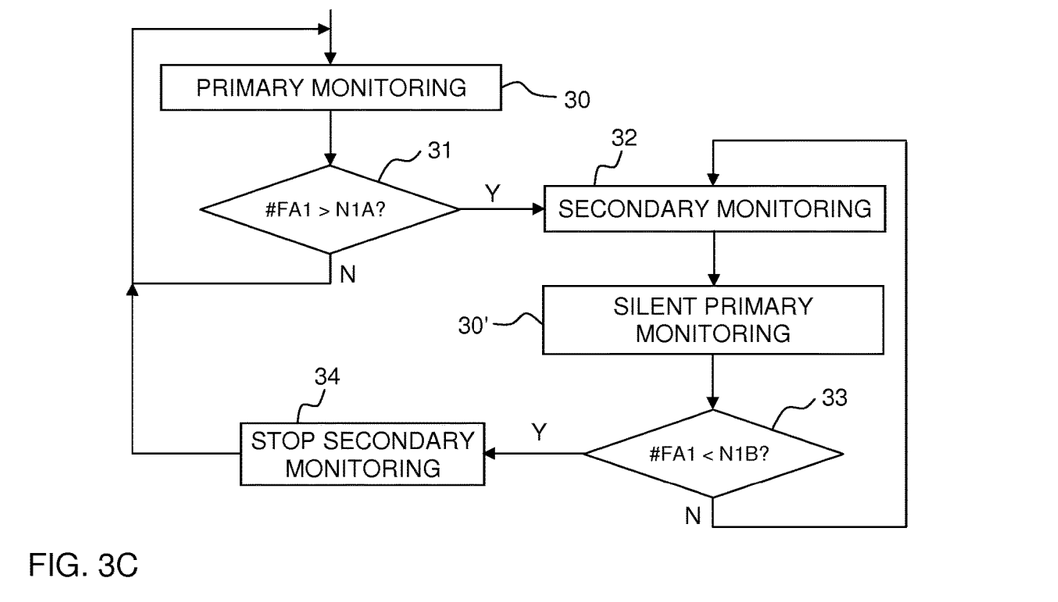

FIGS. 3A-3C are flow charts of different methods of controlling the monitoring device 9. In the illustrated methods, it is presumed that the monitoring device 9 is operated in the first mode by default, and is selectively switched to the second mode, when deemed adequate by the switching module 26. In FIGS. 3A-3C, the first monitoring technique (implemented by the disruption detector 20A and the alarm module 26 in FIG. 2) is denoted "primary monitoring", and the second monitoring technique (implemented by the disruption detector 20B and the alarm module 26 in FIG. 2) is denoted "secondary monitoring".

In the example of FIG. 3A, the monitoring device 9 is operated with only the primary monitoring active in step 30, i.e. the secondary monitoring is not active to generate the alarm signal A. Thus, by step 30, the monitoring device 9 is operated in the first mode. In decision step 31, the number of false alarms #FA1 produced by the primary monitoring in step 30 is evaluated with respect to a predefined limit value N1A. If #FA1 does not exceed N1A, the monitoring device 9 remains in the first mode and the method proceeds to step 30. If step 31 detects that #FA1 exceeds N1A, the method proceeds to step 32 to activate the secondary monitoring, thereby switching the monitoring device 9 to the second mode. As noted above, the primary monitoring 30 may but need not be deactivated in the second mode.

FIG. 3B differs from FIG. 3A by allowing the monitoring device 9 to be switched back from the second mode to the first mode. This is achieved by providing a decision step 33, which compares the number of false alarms #FA2 generated by the secondary monitoring to a predefined limit value N2B. Thus, the provision of step 33 presumes that the disruption detector 20B includes a validation sub-module capable of detecting false alarms and that the FA analyzer 25 is operable to produce the count #FA2 based on the false alarms detected by this validation sub-module. If #FA2 does not exceed N2B, the monitoring device 9 remains in the second mode and the method proceeds to step 32. If step 33 detects that #FA2 exceeds N2B, the method proceeds to step 34 to deactivate the secondary monitoring and then proceeds to iterate through steps 30-31 in the first mode. If the primary monitoring was deactivated during the second mode, then the primary monitoring is activated at step 30. The use of two different parameters, #FA1 and #FA2, for deciding when to switch between the first and second modes may make it somewhat difficult to set the limits N1A, N2B so as to ensure proper operation of the monitoring device 9. Thus, in an alternative embodiment, presuming that both the primary monitoring and the secondary monitoring are active to generate the alarm signal A in the second mode, step 33 may instead compare the count #FA1 to a limit N1B and decide to switch back to the first mode if #FA1 is below N1B. Thus, one and the same parameter, #FA1, is evaluated by steps 31 and 33 when deciding to switch between the first and second modes. In this alternative embodiment, N1B may be simply set equal to N1A. However, to avoid that small changes in #FA1 causes the monitoring device 9 to switch back and forth between the first and second modes, it may be advantageous to introduce a hysteresis in the mode switching, e.g. by setting N1B slightly smaller than N1A. N1B may be set, manually or automatically, to control the tendency of the monitoring device 9 to operate with activated secondary monitoring, since a decrease in N1B (larger hysteresis) increases this tendency. For example, the monitoring device 9 may be configured to set the hysteresis based on patient history, if available, so that a patient with a history of higher than normal frequency of false alarms from the primary monitoring is operated with a larger hysteresis. Thus, the monitoring device 9 may store, e.g. in memory 12 (FIG. 1), patient history including a historic record of the number of false alarms generated by the primary and/or secondary monitoring for each patient. Thus, if the patient is identified to the monitoring device 9, the monitoring device 9 may automatically prioritize between the primary and secondary monitoring based on patient history. As an alternative or supplement to modifying the hysteresis, the FA analyzer 25 may be configured to account for the patient history when generating #FA1 or #FA2 for use by step 33, so to thereby control the tendency of the monitoring device 9 to operate with activated secondary monitoring. For example, for a patient with a history of frequent false alarms from the primary monitoring, the FA analyzer 25 may add an offset to the actual number of false alarms when generating #FA1 or subtract an offset from the actual number of false alarms when generating #FA2, for use in step 33. The same effect may be achieved by the FA analyzer 25 subtracting an offset from #FA1, for use step 31. The skilled person realizes that the opposite changes may be made to reduce the tendency of the monitoring device 9 to operate with activated secondary monitoring.

FIG. 3C illustrates an embodiment in which only the secondary monitoring is active to generate the alarm signal A in the second mode, but both decision steps 31, 33 operate on #FA1 to decide when to switch from the first mode to the second mode, and from the second mode to the first mode, respectively. This embodiment is enabled by step 30', which sets the primary monitoring to a "silent state" in the second mode. In the silent state, the primary monitoring is operated to provide alarm indications, so that the count #FA1 of false alarms can be acquired and evaluated in step 33, but the alarm indications from the primary monitoring do not impact the generation of the alarm signal A. Thus, the primary monitoring is merely operated for the purpose of determining a proper time point for switching back to the first mode. As indicated in step 33 of FIG. 3C, the method may decide to switch back to the first mode if #FA1 is below N1B. The limits N1A, N1B may be set as discussed above in relation to FIG. 3B. In the monitoring device 9 of FIG. 2, the silent state may be achieved in many different ways. In one example, the switching module 26 may set, by control signal C4, the validation sub-module 23A' to not provide true alarm indications to the alarm module 24. In another example, the switching module 26 may set, by control signal C2, the alarm module 24 to not consider true alarm indications provided by the validation sub-module 23A'.

Figure 3D:
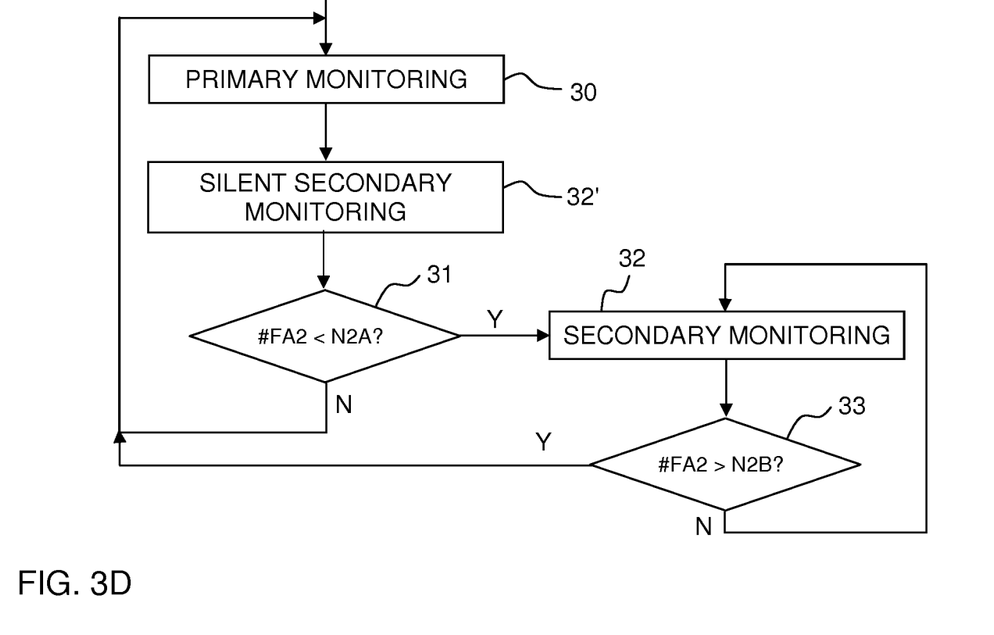

FIG. 3D illustrates variant of the embodiment in FIG. 3B. The secondary monitoring is set in a silent state in the first mode, by a step 32', and decision steps 31, 33 operate on #FA2 to decide when to switch from the first mode to the second mode, and from the second mode to the first mode, respectively. In the silent state, in analogy with FIG. 3C, the secondary monitoring is operated to provide alarm indications, so that the count #FA2 of false alarms can be acquired and evaluated in step 31, but the alarm indications from the secondary monitoring do not impact the generation of the alarm signal A. Thus, one and the same parameter, #FA2, is evaluated by steps 31 and 33 when deciding to switch between the first and second modes. As indicated in step 33 of FIG. 3D, the method may decide to switch back to the first mode if #FA2 exceeds N2B. The limits N2A, N2B may be set equal, or N2A may be set slightly larger than N2B. In an alternative embodiment, presuming that both the primary monitoring and the secondary monitoring are active to generate the alarm signal A in the second mode, step 33 may instead compare the count #FA1 to a limit N1B and decide to switch back to the first mode if #FA1 is below N1B.

In a variant of the embodiments in FIGS. 3B-3D, decision step 33 may evaluate both #FA1 and #FA2 to decide when to switch from the second mode to the first mode. Alternatively or additionally, in the embodiment of FIG. 3D, decision step 31 may evaluate both #FA1 and #FA2 to decide when to switch from the first mode to the second mode.

In a further variant of the embodiments in FIGS. 3B-3D, the decision step 33 directs the method to activate a third monitoring technique to monitor the fluid connection and generate the alarm signal A instead of, or in combination with, the first and/or second monitoring techniques. Thus, in such a variant, the monitoring device 9 is switched between first, second and third modes.

In all embodiments described herein, the monitoring device 9 may be configured generate the alarm signal A if the number of switches between the primary and secondary monitoring per unit time exceeds a predefined limit. To remedy this situation, the operator may be instructed to modify one of the limits N1A, N1B, N2A, N2B that are used by the decision steps 31, 33. Alternatively or additionally, the monitoring device 9 may deactivate both of the first and second monitoring techniques and inform the operator accordingly, e.g. by generating the alarm signal A. Alternatively or additionally, the monitoring device 9 may activate a third monitoring technique instead of the first and second monitoring techniques.

In all embodiments described herein, the monitoring device 9 may be configured to also switch between the first and second modes based on operational data of the apparatus 1, e.g. when the operational data indicate that disturbances are likely to occur in one or more measurement signals so as to cause the primary or secondary monitoring to generate false alarms. Such situations may, e.g., occur for certain blood flows, when the apparatus 1 is set in a particular operating mode, or when a known source of interference is activated in the apparatus 1. Thus, the switching is made to temporarily, during the disturbance, deactivate the monitoring technique that is known to be sensitive to the disturbance so as to forestall the generation of false alarms by this monitoring technique. Suitably, the monitoring device 9 is also operated to ensure that the count of false alarms for the deactivated monitoring technique is not updated during the temporary switch, e.g. by deactivating the corresponding disruption detector 20A, 20B, or by selectively controlling the FA analyzer 25.

Figure 4:
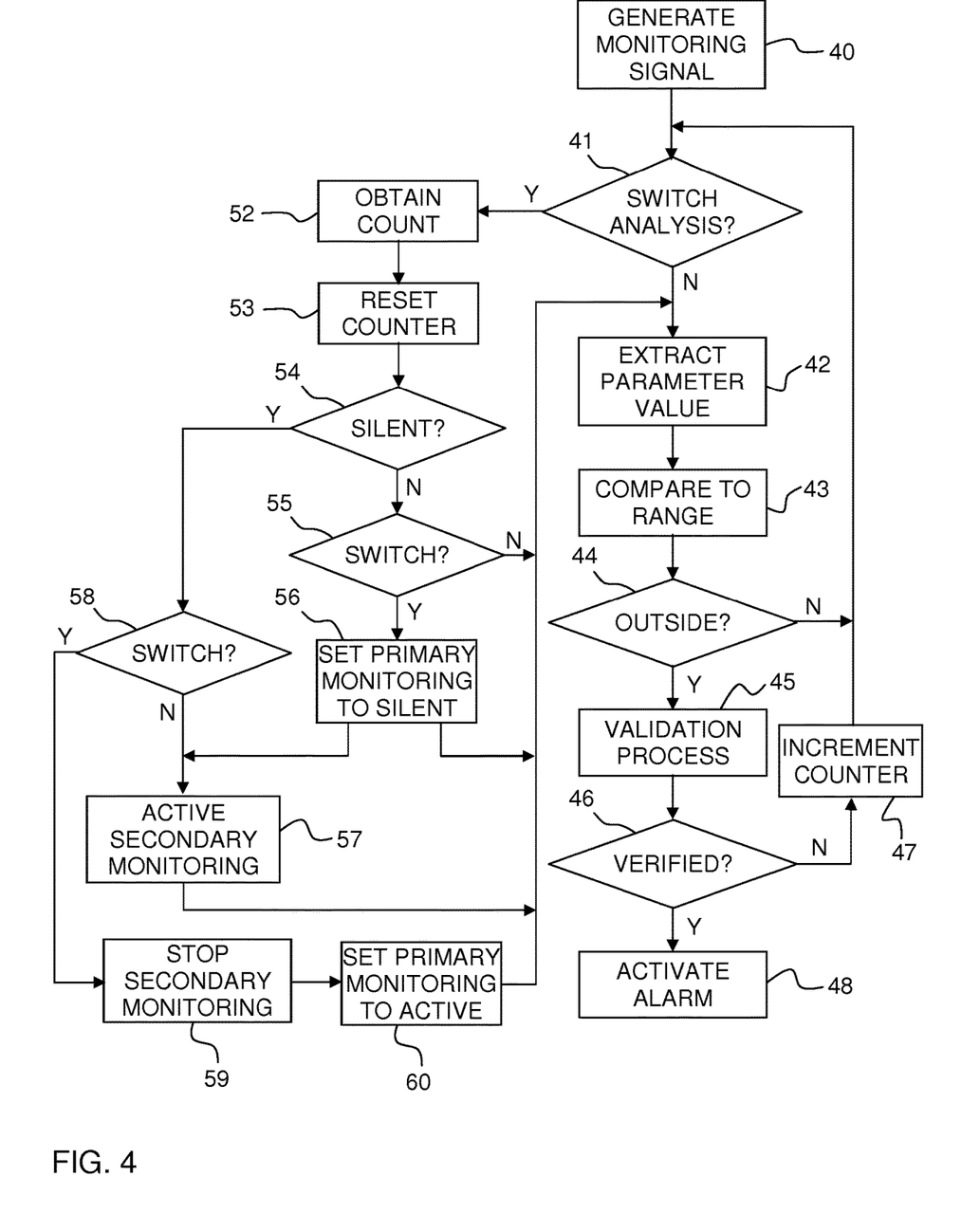
FIG. 4 is a flow chart of a detailed implementation of the monitoring process in FIG. 3C.

FIG. 4 illustrates a more detailed implementation example of the method in FIG. 3C. Thus, method in FIG. 4 is designed to automatically switch from the first mode (active primary monitoring and non-active secondary monitoring) to the second mode (active secondary monitoring and primary monitoring in silent state) when the primary monitoring produces an unacceptable number of false alarms, and then switch back to the first mode when the primary monitoring is found to produce an acceptable number of false alarms. In FIG. 4, the primary monitoring is represented by steps 40-48. In the context of FIG. 2, step 40 is executed by sub-module 21A, step 41 is executed by module 26, step 42 is executed by sub-module 22A, steps 43-44 are executed by module 23A, steps 45-46 are executed by module 23A', and step 48 is executed by module 24. Step 40 generates the monitoring signal $M_A$ and typically operates continuously to generate a sequence of signal values at a fixed or variable rate while the primary monitoring repeatedly proceeds through steps 41-48 to detect and signal a disruption based on the signal values. Step 41 determines if a switch analysis should be initiated. Step 41 may e.g. initiate the switch analysis at fixed time intervals. If no switch analysis is due, the process proceeds to step 42 which extracts or computes a parameter value from the monitoring signal $M_A$. Step 43 compares the parameter value to an allowable range. If the parameter value falls outside the allowable range, step 44 generates an alarm indication and proceeds to step 45 which initiates the automatic validation. Otherwise, step 44 proceeds to step 41. Step 44 may apply an additional detection criterion before proceeding to step 45, e.g. that a predefined number of consecutive parameter values fall outside the allowable range or that a predefined number parameter values within a given time period fall outside the allowable range. If the alarm indication is not verified as true by the automatic validation, step 46 directs the process to step 47, which increments a counter of false alarms (which is set to zero at startup of the process), and then to step 41. If the alarm indication is verified, step 46 directs the process to step 48, which generates the alarm signal.

The switch analysis, when initiated by step 41, obtains a current count #FA1 of false alarms from the counter of false alarms (step 52) and then resets the counter (step 53) and proceeds to decision step 54 which bifurcates the switch analysis depending on the current state of the primary monitoring. The state may be either "active" or "silent". If in active state, the primary monitoring is operating and configured to activate the alarm signal based on true alarm indications from step 46. If in silent state, the primary monitoring is operating and configured not to activate the alarm signal. If the primary monitoring is in active state at step 54, the process proceeds to decision step 55 which compares the current count #FA1 to a first limit N1. If the current count #FA1 is smaller than the first limit N1, the primary monitoring remains in the active state and the process proceeds to step 42. If the current count #FA1 is larger than the first limit N1, the primary monitoring is switched to silent state (step 56) and proceeds to step 42. Further, the secondary monitoring is activated (step 57), so that the primary monitoring and the secondary monitoring are operated in parallel. Steps of the secondary monitoring is not disclosed in detail, but the skilled person realizes that the secondary monitoring may comprise steps corresponding to at least steps 40, 42, 43, 44 and 48. If the primary monitoring is in silent state at step 54, the process proceeds to decision step 58 which compares the current count #FA1 to a second limit N2. If the current count #FA1 is larger than the second limit N2, the secondary monitoring remains active (step 57) and method proceeds to step 42 with the primary monitoring remaining in the silent state. If the current count #FA1 is smaller than the second limit N2, the secondary monitoring is stopped (step 59), the primary monitoring is set in the alarm state (step 60) and the method proceeds to step 42. In the context of FIG. 2, steps 52 and 54-60 are executed by module 26, and step 53 is executed by module 25.

In a variant of the method in FIG. 4, the decision step 41 initiates the switch analysis based on the current count #FA1 instead of at fixed time intervals. This may be achieved by incorporating steps 52-55 and 58 into step 41. In such a variant, the decision step 41 may proceed directly to one of steps 56, 57 and 59 depending on the outcome of the decision steps 54, 55 and 58 as implemented by step 41.

As understood from the foregoing, the primary and secondary monitoring techniques may be selected among any available techniques for detecting a disruption or disconnection of a fluid connection between two fluid containing systems, including known VND techniques. Two such VND techniques will be briefly exemplified below with reference to FIGS. 5-6, in the context of the apparatus 1 in FIG. 1. One of these VND techniques is denoted VPM ("Venous Pressure Monitoring") herein and is conventionally used in safety systems of dialysis machines. The other VND technique is denoted PPM ("Pressure Pulse Monitoring") herein. In the following examples, it is assumed that the disruption detectors 20A, 20B in FIG. 2 implement the PPM technique and the VPM technique, respectively.

Figure 5:
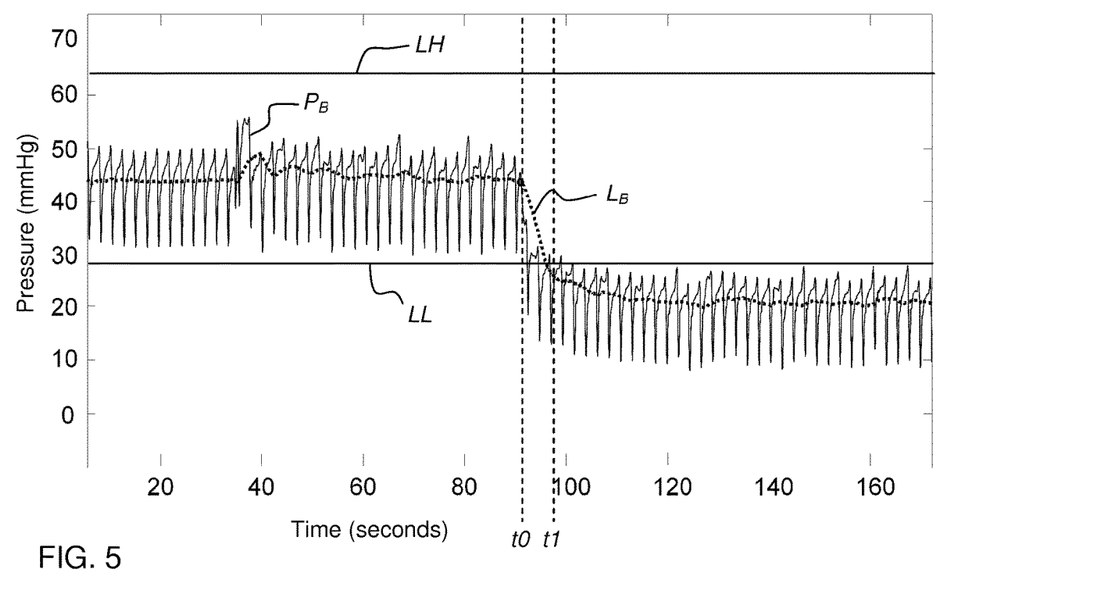
FIG. 5 illustrates VND detection based on pressure level monitoring.

The VPM technique is based on the principle that a venous-side disruption ("VND event") results in a change in blood pressure measured by the venous sensor 8a. If the access device 2" is detached from the vascular access 3 without changing the vertical position (altitude) of the access device 2", the change in venous pressure is equal to the access pressure, i.e. the pressure in the vascular access 3. This principle is exemplified in FIG. 5, in which a VND event occurs at time point t0. FIG. 5 illustrates the venous signal $P_B$ obtained from the venous pressure sensor 8a. As seen, the venous signal $P_B$ exhibits strong pulsations that originate from the operation of the blood pump 4, in this example a peristaltic pump. To facilitate detection of the pressure change, the venous signal $P_B$ is processed, e.g. by filtering, for extraction of parameter values $L_B$ that represent the pressure level on the venous side of the EC circuit 1a. The parameter values $L_B$ are compared to an allowable range which may be defined by a lower limit LL, where an alarm indication is generated at time t1 in FIG. 5, when a count of consecutive parameter values $L_B$ that fall below the lower limit LL is found to exceed a predefined number limit. To avoid missing an alarm situation when the parameter values L fluctuate around the lower limit LL, a hysteresis may be introduced in the detection by adding a second lower limit (not shown) slightly above the lower limit LL. With such a hysteresis, the counting of consecutive parameter values L may start at the time point when a parameter value is found to fall below the lower limit LL and continue as long as the subsequent consecutive parameter values remain below the second lower limit. As indicated in FIG. 5, an upper limit LH may also be set for detection of malfunctions that cause an increase in venous-side pressure, such as infiltration. Further, the upper limit LH may be set to detect a situation in which the venous-side pressure increases when the access device 2" is detached from the vascular access 3, e.g., if the detached access device 2" gets stuck in the bedclothes or the clothes of the patient or if the detached access device 2" ends up at a higher altitude than the vascular access 3 (thereby increasing the hydrostatic pressure on the venous side). Conventionally, the limits LL, LH are set, automatically by the main control unit of the apparatus 1 or manually by an operator, and subsequently acknowledged by the operator at the beginning of blood treatment and may remain fixed throughout the blood treatment. The apparatus 1 may allow the operator to manually change the limits LL, LH during blood treatment, and the main control unit of the apparatus 1 may automatically change the limits LL, LH when the blood flow in the EC circuit 1a is changed. It is also known from U.S. Pat. No. 7,575,562 to adjust the location of the allowable range with respect to the current signal level in the venous signal at well-defined time intervals, so that the allowable range follows natural variations in the venous pressure signal while ensuring that a VND event is accurately detected. Similarly, JP2010-136745 proposes to update the location of the allowable range based on concurrent changes in an arterial signal generated by an arterial pressure sensor in the EC circuit (cf. 8b in FIG. 1). It is also known to generate the parameter values $L_B$ to represent a combination of the venous and arterial signals. For example, US2011/0034814 proposes to generate the parameter values $L_B$ to represent a pressure differential between the venous and arterial signals, for the purpose of reducing the impact of patient movement on the parameter values $L_B$.

The PPM technique is based on the principle that a VND event results in a decrease or disappearance in the venous signal of pressure pulsations ("target pulses") that represent pressure waves that have propagated through the fluid connection that is monitored for disruption. The pressure waves may originate from a pulse generator associated with the patient, e.g. a physiological pulse generator PH (FIG. 1) in the patient, such as the heart or the breathing system, or a separate device attached to the patient. Different implementations of the PPM technique are, e.g., described in U.S.

Pat. No. 6,090,048, WO2009/156174, WO2010/149726, US2005/0010118 and WO2011/080193. In a variant of the PPM technique, proposed in WO2012/175267, the arterial signal is analyzed for detection of target pulses that originate from the blood pump and have propagated through the vascular access to the arterial sensor.

The PPM technique may involve a filtering of the venous signal to suppress interfering signal artifacts, such as pulsations caused by the blood pump 4, while retaining the target pulses. The resulting monitoring signal $M_A$ is then processed for extraction of parameter values $L_A$ of a detection parameter that represents the magnitude of the target pulses, and the parameter values $L_A$ are compared to an allowable range, in analogy with the discussion in relation to FIG. 5. Many different detection parameters are known in the art, e.g. (average) magnitude of pulsations in the monitoring signal, a variability of signal values within a time window in the monitoring signal, a correlation coefficient obtained by correlating the monitoring signal with a reference signal, a magnitude of a frequency component in a frequency spectrum obtained by frequency analysis of the monitoring signal, etc.

Figure 6A:
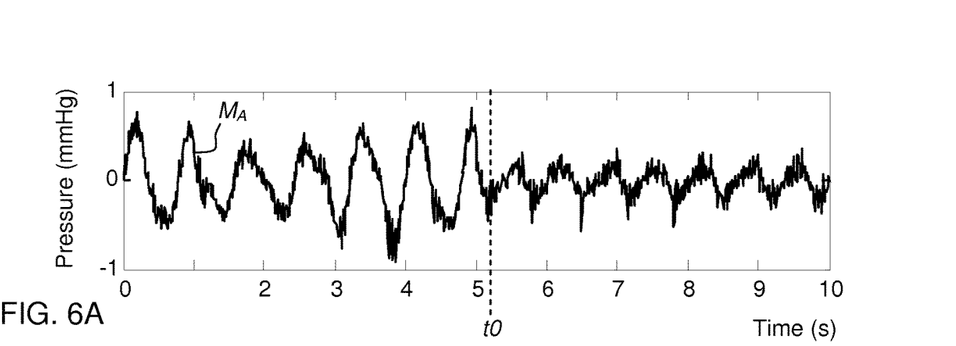
FIGS. 6A-6B illustrate VND detection based on pressure pulsation monitoring.
Figure 6B:
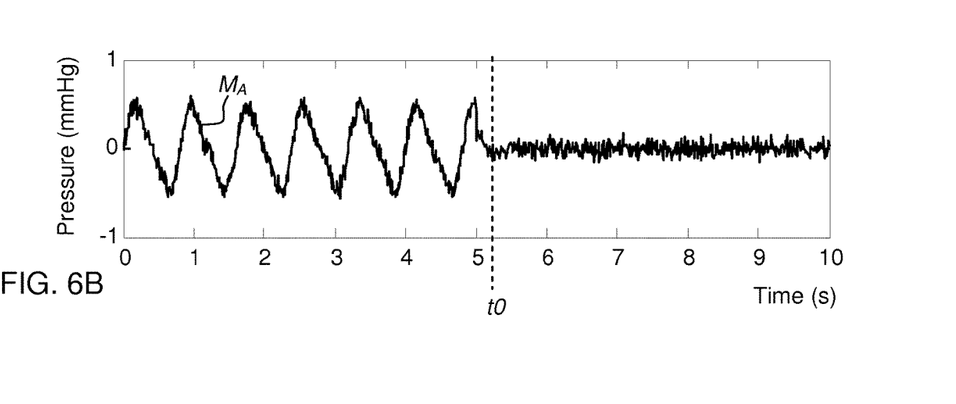

The PPM technique is further exemplified in FIG. 6A, which illustrates a monitoring signal $M_A$ obtained by filtering a venous signal which is obtained during operation of a blood processing apparatus 1. The monitoring signal $M_A$ includes target pulses, which disappear at time point t0 when a VND event occurs. As seen in FIG. 6A, weak pulsations remain in the monitoring signal after the VND event. The weak pulsations are residuals of the signal artifacts that are suppressed by the filtering, specifically pulsations originating from the blood pump 4. FIG. 6B illustrates a corresponding monitoring signal $M_A$ obtained when the blood pump 4 has been disabled (stopped). As seen, by disabling the blood pump 4, the residuals disappear in the monitoring signal $M_A$ and detection of a disappearance of the target pulses is facilitated.

It should be understood that the blood pump 4 is normally active during operation of the apparatus 1 and thus also during operation of the monitoring device 9. However, as noted with reference to FIG. 2, the validation sub-module 23A' may be configured to, upon generation of an alarm indication by the analyzer 23A, intermittently disable the blood pump 4 (by control signal C1) and possibly at least part of the filtering by the preprocessor 21A. If the analyzer 23A then generates another alarm indication within a given time period, the sub-module 23A' may conclude that the alarm indication is true, otherwise false.

It should be noted that an alarm indication provided by the VPM technique may likewise be validated by disabling the blood pump 4 and analyzing the venous pressure signal for disappearance of target pulses. Thus, a validation sub-module for the disruption detector 20B may be configured to, upon generation of an alarm indication by the analyzer 23B, intermittently disable the blood pump 4 and at least part of the filtering by the preprocessor 21B, and modify the extractor 22B and the analyzer 23B to generate and evaluate, respectively, parameter values $L_B$ of a detection parameter which is indicative of presence or absence of target pulses in the monitoring signal $M_B$. If the analyzer 23B then generates another alarm indication within a given time period, the validation sub-module may conclude that the alarm indication is true, otherwise false.

The PPM and VPM techniques are at least partly complementary and may thus be used as primary and secondary monitoring techniques in embodiments of the invention. The PPM technique may generate false alarms when the rate of target pulses essentially coincides with a frequency component of signal interferences in the venous signal, e.g. pulsations caused by the blood pump 4. The risk for false alarms is also elevated if the target pulses are weak compared to the residuals in the monitoring signal (cf. FIG. 6A). The VPM technique, on the other hand, is essentially unaffected by these factors, but instead suffer from being sensitive to patient movement and a risk of false negatives. Therefore, based on the risk for false negatives, it may be preferable for the primary (default) monitoring to be a PPM technique and the secondary monitoring a VPM technique. However, it is conceivable that the primary monitoring is a VPM technique and the secondary monitoring is a PPM technique. In yet other alternatives, both of the primary and secondary monitoring may be different variants of either the VPM technique or the PPM technique.

The monitoring device 9 as described herein may be implemented by special-purpose software (or firmware) run on one or more general-purpose or special-purpose computing devices. In this context, it is to be understood that a "module" or "means" of such a computing device refers to a conceptual equivalent of a method step; there is not always a one-to-one correspondence between modules/means and particular pieces of hardware or software routines. One piece of hardware sometimes comprises different modules/means. For example, a processing unit serves as one module/means when executing one instruction, but serves as another module/means when executing another instruction. In addition, one module/means may be implemented by one instruction in some cases, but by a plurality of instructions in some other cases. Such a software controlled computing device may include one or more processing units (cf. 11 in FIG. 1), e.g. a CPU ("Central Processing Unit"), a DSP ("Digital Signal Processor"), an ASIC ("Application-Specific Integrated Circuit"), discrete analog and/or digital components, or some other programmable logical device, such as an FPGA ("Field Programmable Gate Array"). The device 9 may further include a system memory (cf. 12 in FIG. 1) and a system bus that couples various system components including the system memory to the processing unit. The system bus may be any of several types of bus structures including a memory bus or memory controller, a peripheral bus, and a local bus using any of a variety of bus architectures. The system memory may include computer storage media in the form of volatile and/or non-volatile memory such as read only memory (ROM), random access memory (RAM) and flash memory. The special-purpose software may be stored in the system memory, or on other removable/non-removable volatile/non-volatile computer storage media which is included in or accessible to the computing device, such as magnetic media, optical media, flash memory cards, digital tape, solid state RAM, solid state ROM, etc. The device 9 may include one or more communication interfaces (cf. 10 in FIG. 1), such as a serial interface, a parallel interface, a USB interface, a wireless interface, a network adapter, etc, as well as one or more data acquisition devices, such as an A/D converter. The special-purpose software may be provided to the device 9 on any suitable computer-readable medium, transitory or non-transitory, including a record medium or a read-only memory.

It is also conceivable that some (or all) elements/means are fully or partially implemented by dedicated hardware, such as an FPGA, an ASIC, or an assembly of discrete electronic components (resistors, capacitors, operational amplifier, transistors, filters, etc), as is well-known in the art.

It should be emphasized that the invention is not limited to digital signal processing, but could be fully implemented by a combination of analog devices.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

For example, the inventive monitoring is applicable to fluid systems that contain other liquids than blood and are connected to the cardiovascular system of a human or animal subject, including systems for intravenous therapy, infusion systems, automated peritoneal dialysis (APD) systems, etc. Examples of such liquids include medical solutions, dialysis fluids, infusion liquids, water, etc.

It should be emphasized that the fluid containing systems need not involve a human or animal subject. For example, the inventive monitoring technique may be used to detect a disruption of a fluid connection between two machines or between a machine and a container.

The invention claimed is:

1. A monitoring device, comprising:
   an input interface for receiving one or more measurement signals from one or more sensors arranged in or associated with a first fluid containing system and/or a second fluid containing system, the one or more measurement signals being responsive to a disruption of a fluid connection between the first fluid containing system and the second fluid containing system,
   a first disruption detector and a second disruption detector, each being configured to operate a respective detection logic on at least one of the one or more measurement signals to detect apparent disruptions of the fluid connection and provide alarm indications corresponding to the apparent disruptions,
   an alarm module for generating an alarm signal based on the alarm indications, and
   a switching module configured to operate the monitoring device in one of a first mode, in which at least the first disruption detector is operated and the alarm signal is generated based only on the alarm indications provided by the first disruption detector, and a second mode, in which at least the second disruption detector is operated and the alarm signal is based at least on the alarm indications provided by the second disruption detector,
   wherein the switching module is configured to, when operating the monitoring device in the first mode, obtain at least one of a first count of false alarm indications provided per unit time by the first disruption detector and a second count of false alarm indications provided per unit time by the second disruption detector, and selectively, based on at least one of the first and second counts, switch the monitoring device to the second mode.

2. The monitoring device of claim 1, wherein the switching module is configured to switch the monitoring device from the first mode to the second mode when the first count exceeds a predefined first limit and/or when the second count is below a predefined second limit.

3. The monitoring device of claim 1, wherein the switching module is configured to, when operating the monitoring device in the second mode, operate the first disruption detector and the second disruption detector to provide the alarm indications, obtain at least one of the first and second counts, and selectively, based on the at least one of the first and second counts, switch the monitoring device to the first mode.

4. The monitoring device of claim 3, wherein the switching module is configured to selectively switch the monitoring device from the second mode to the first mode when the first count is below a predefined second limit and/or when the second count exceeds a predefined fourth limit.

5. The monitoring device of claim 1, wherein the switching module is configured to operate the monitoring device in the second mode so that the alarm signal is generated based only on the alarm indications provided by the second disruption detector.

6. The monitoring device of claim 1, wherein the switching module is configured to operate the monitoring device in the second mode so that the alarm signal is generated based on the alarm indications provided by the second disruption detector and the alarm indications provided by the first disruption detector.

7. The monitoring device of claim 1, wherein each of the first and second disruption detectors is configured to, when operating the respective detection logic, generate a time-sequence of parameter values of a detection parameter to represent a time segment in the at least one measurement signal, compare the time-sequence of parameter values to an allowable range, and provide the alarm indications when a predefined number of parameter values in the time-sequence of parameter values fall outside the allowable range.

8. The monitoring device of claim 7, wherein the detection logics of the first and second disruption detectors differ by at least one of: the at least one measurement signal, preprocessing of the at least one measurement signal, the detection parameter, the current allowable range, and the predefined number of parameter values.

9. The monitoring device of claim 7, wherein the second disruption detector is configured to obtain the at least one measurement signal from at least one pressure sensor in the first fluid containing system, and generate the time-sequence of parameter values to be indicative of a pressure level in the first fluid containing system.

10. The monitoring device of claim 7, wherein the first disruption detector is configured to obtain the at least one measurement signal from at least one pressure sensor in the first fluid containing system, and generate the time-sequence of parameter values to represent pulsations originating from a pulse generator in or associated with the second fluid containing system.

11. The monitoring device of claim 1, wherein the first disruption detector is configured to perform an automatic validation of each alarm indication to determine the alarm indication as a false alarm indication or a true alarm indication, and wherein the monitoring device comprises a false alarm analyzer configured to produce the first count based on the false alarm indications determined by the automatic validation.

12. The monitoring device of claim 11, wherein the automatic validation involves one or more of: obtaining and processing a further measurement signal among the one or more measurement signals; generating parameter values of another detection parameter as a function of the at least one measurement signal; and intermittently disabling one or more sources of signal interferences in the at least one measurement signal.

13. The monitoring device of claim 11, wherein the first fluid containing system comprises a blood processing apparatus for connection, by the fluid connection, to a subject, wherein the one or more sensors comprise a pressure sensor for sensing a pressure of blood in the blood processing apparatus, wherein the automatic validation comprises: obtaining and processing the at least one measurement signal for detection of pulsations originating from a pulse generator in or associated with the subject.

14. The monitoring device of claim 13, wherein the automatic validation comprises, before obtaining and processing the at least one measurement signal, generating a control signal to stop one or more pumping devices arranged in the blood processing apparatus.

15. The monitoring device of claim 11, wherein the alarm module is configured to generate the alarm signal based on the true alarm indications.

16. An apparatus for extracorporeal blood processing, comprising:
   an extracorporeal blood circuit for connection in fluid communication with the vascular system of a patient at first and second ends and comprising a blood pump for circulating blood from the first end through a blood processing device to the second end;
   at least one sensor configured to generate at least one measurement signal which is responsive to a disconnection of the extracorporeal blood circuit from the vascular system of the patient downstream of the blood pump;
   a first disruption detector and a second disruption detector, each being configured to operate a respective detection logic on at least one of the one or more measurement signals to detect the disconnection and provide an alarm indication corresponding to the disconnection,
   an alarm module for generating an alarm signal based on the alarm indication, and
   a switching module configured to operate the monitoring device in one of a first mode, in which at least the first disruption detector is operated and the alarm signal is generated based only on the alarm indication provided by the first disruption detector, and a second mode, in which at least the second disruption detector is operated and the alarm signal is generated based at least on the alarm indication provided by the second disruption detector,
   wherein the switching module is configured to, when operating the monitoring device in the first mode, obtain at least one of a first count of false alarm indications provided per unit time by the first disruption detector and a second count of false alarm indications provided per unit time by the second disruption detector, and selectively, based on at least one of the first and second counts, switch the monitoring device to the second mode.

17. A method of detecting a disruption of a fluid connection between two fluid containing systems, the method comprising:
   activating a first monitoring technique that operates to detect the disruption and generate a corresponding alarm signal while a second monitoring technique is deactivated,
   obtaining at least one of a first count of false alarms generated by the first monitoring technique and a second count of false alarms generated by the deactivated second monitoring technique in a silent state, and
   selectively, based on at least one of the first and second counts, activating the second monitoring technique to operate, instead of or jointly with the first monitoring technique, to detect the disruption and generate the corresponding alarm signal.

18. The method of claim 17, wherein the second monitoring technique is selectively activated when the first count exceeds a predefined first limit and/or when the second count is below a predefined second limit.

19. The method of claim 17, comprising: selectively, based on at least one of the first and second counts, deactivating the second monitoring technique.

20. The method of claim 19, wherein the second monitoring technique is selectively deactivated when the first count is below a predefined third limit and/or when the second count exceeds a predefined fourth limit.

21. The method of claim 17, comprising: setting the first monitoring technique into a silent state while the second monitoring technique is activated, the silent state causing the first monitoring technique to operate to detect the disruption without generating the corresponding alarm signal, the method comprising: evaluating if a respective disruption detected by the first monitoring technique in the silent mode represents a false alarm and updating the first count accordingly.

22. The method of claim 17, wherein the deactivated second monitoring technique in the silent state operates to detect the disruption without generating the corresponding alarm signal, the method comprising: evaluating if a respective disruption detected by the second monitoring technique in the silent state represents a false alarm and updating the second count accordingly.

23. The method of claim 17, comprising: validating a respective disruption detected by the first monitoring technique to identify the respective disruption as a false alarm indication or a true alarm indication, and generating the first count based on the thus-identified false alarm indications.

24. The method of claim 23, wherein the validating comprises: intermittently stopping operation of one or more devices in the first and/or second fluid containing system, the devices causing, when operating, signal interferences in one or more measurement signals that are processed by the first monitoring technique for detection of the disruption.

25. The method of claim 17, comprising: validating a respective disruption detected by the second monitoring technique to identify the respective disruption as a false alarm indication or a true alarm indication, and generating the first count based on the thus-identified false alarm indications.

26. The method of claim 17, wherein each of the first and second monitoring techniques operates on one or more measurement signals from one or more sensors arranged in or associated with the first fluid containing system and/or the second fluid containing system, the one or more measurement signals being responsive to the disruption of the fluid connection, the method comprising obtaining the one or more measurement signals.

27. The method of claim 17, comprising: obtaining at least one pressure signal from at least one pressure sensor in the first fluid containing system, wherein the first monitoring technique, to detect the disruption, operates on the at least one pressure signal to generate a time-sequence of parameter values that represent pulsations originating from a pulse generator in or associated with the second fluid containing system, and compares the parameter values to an allowable range.

28. The method of claim 17, comprising: obtaining at least one pressure signal from at least one pressure sensor in the first fluid containing system, wherein the second monitoring technique, to detect the disruption, operates on the at least one pressure signal to generate a time-sequence of parameter values that are indicative of a pressure level in the first fluid containing system, and compares the parameter values to an allowable range.

29. A method of controlling a monitoring device comprising a processor, the method being executed by the processor in the monitoring device and comprising:

obtaining one or more measurement signals from one or more sensors arranged in or associated with a first fluid containing system and/or a second fluid containing system, the one or more measurement signals being responsive to a disruption of a fluid connection between the first fluid containing system and the second fluid containing system, generating, in a first operating mode of the monitoring device, an alarm signal based only on alarm indications provided by a first detection logic when operated on at least one of the one or more measurement signals to detect apparent disruptions of the fluid connection, obtaining, when operating the monitoring device in the first mode, at least one of a first count of false alarm indications provided per unit time by the first detection logic and a second count of false alarm indications provided per unit time by a second detection logic, and selectively, based on at least one of the first and second counts, switching the monitoring device to a second mode, in which the alarm signal is generated based at least on alarm indications provided by the second detection logic.

* * * * *